US00PP36537P2

(12) United States Plant Patent
Alt

(10) Patent No.: US PP36,537 P2
(45) Date of Patent: Mar. 11, 2025

(54) APPLE TREE NAMED 'SA 1088'

(50) Latin Name: *Malus domestica*
Varietal Denomination: SA 1088

(71) Applicant: Steve Alt, Comstock Park, MI (US)

(72) Inventor: Steve J. Alt, Comstock Park, MI (US)

( * ) Notice: Subject to any disclaimer, the term of this patent is extended or adjusted under 35 U.S.C. 154(b) by 0 days.

(21) Appl. No.: 18/445,544

(22) Filed: Oct. 10, 2023

(51) Int. Cl.
*A01H 5/08* (2018.01)
*A01H 6/74* (2018.01)

(52) U.S. Cl.
USPC ..... Plt./162

(58) Field of Classification Search
USPC ..... Plt./161, 162
See application file for complete search history.

*Primary Examiner* — Susan McCormick Ewoldt

(57) ABSTRACT

A new and distinct variety of Gala apple tree, named 'SA 1088' originating as a whole tree mutation of the *Malus domestica* variety of 'Baigent' (U.S. Plant Pat. No. 10,016). This new variety is unique from its parent cultivars in the solid red blush coloration of the fruit, the intense red coloration of the leaf petiole, the bright red blush of the blossom buds and the fruit ripening period which is 5 days ahead of the parent and other Gala.

2 Drawing Sheets

Latin name of the genus and species of the plant claimed: *Malus domestica.*

Variety denomination: 'SA 1088'.

DESCRIPTIONS OF RELATED APPLICATIONS

The new variety, 'SA 1088' differs from its parent, 'Baigent' (U.S. Plant Pat. No. 10,016) and other Gala varieties in the following characteristics:

A. The new variety differs from its parent 'Baigent' (U.S. Plant Pat. No. 10,016), 'Gale' (U.S. Plant Pat. No. 10,114), Simmons, (U.S. Plant Pat. No. 10,840) and (Ultima, U.S. Plant Pat. No. 13,753) in the solid red blush coloration of the fruit, the red striping on the leaf petiole and midvein and in the intense pink coloration of the blossom. buds and blossoms and the ripening period which is 5 days earlier.

B. The new variety differs from other Gala cultivars in the solid red blush coloration of the fruit, the red coloration on the leaf petiole and midvein and in the intense pink coloration of the blossom buds and blossoms and the ripening date which is 5 days earlier

BACKGROUND OF THE INVENTION

A new and distinct variety of gala apple tree origination as a whole tree mutation of the *Malus domestica* variety of 'Baigent' (U.S. Plant Pat. No. 10,016) hereinafter referred to as the 'SA 1088'. This new sport is unique from its parent and other Gala cultivars in the solid red blush coloration of the fruit, the red coloration on the leaf petiole and midvein and in the intense pink coloration of the blossom buds and blossoms and the ripening date which is 5 days earlier.

SUMMARY OF THE INVENTION

This new and distinct variety of Gala apple tree was discovered in 2012 as a whole tree mutation of 'Baigent' (U.S. Plant Pat. No. 10,016), in an orchard planted in 2010 near Comstock Park, MI. The new variety was noticed because the fruit had a more intense red blush coloration; the buds and blossoms exhibited more pink coloration than the parent, 'Baigent' (U.S. Plant Pat. No. 10,016) and the fruit ripening period was 5 days ahead of the parent.

Observations during the next two seasons confirmed that the fruit colored with intense red blush coloration as opposed to the parent which colors with a fine stripe. The blossoms and blossom buds of the new variety exhibited a much higher degree of pink coloration than the parent.

In April of 2013, dormant scions were taken from the original tree and trees for further testing were reproduced by grafting these scions onto adjacent trees. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained in Comstock Park, Kent County, MI, 49345.

DETAILED BOTANICAL DESCRIPTION

Figure 1:
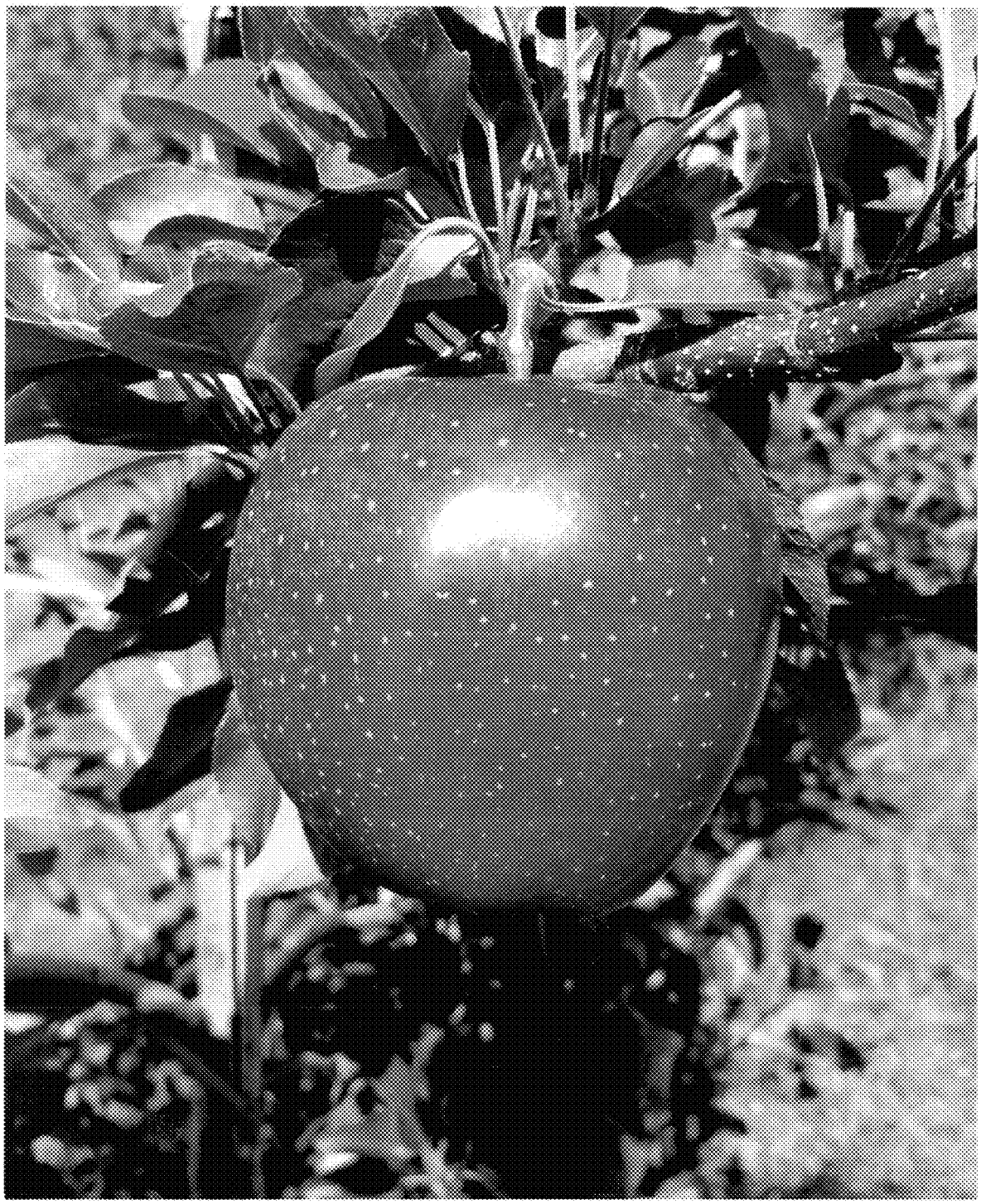
FIG. 1 illustrates the fruit, petioles and foliage of the new variety at maturity.
Figure 2:
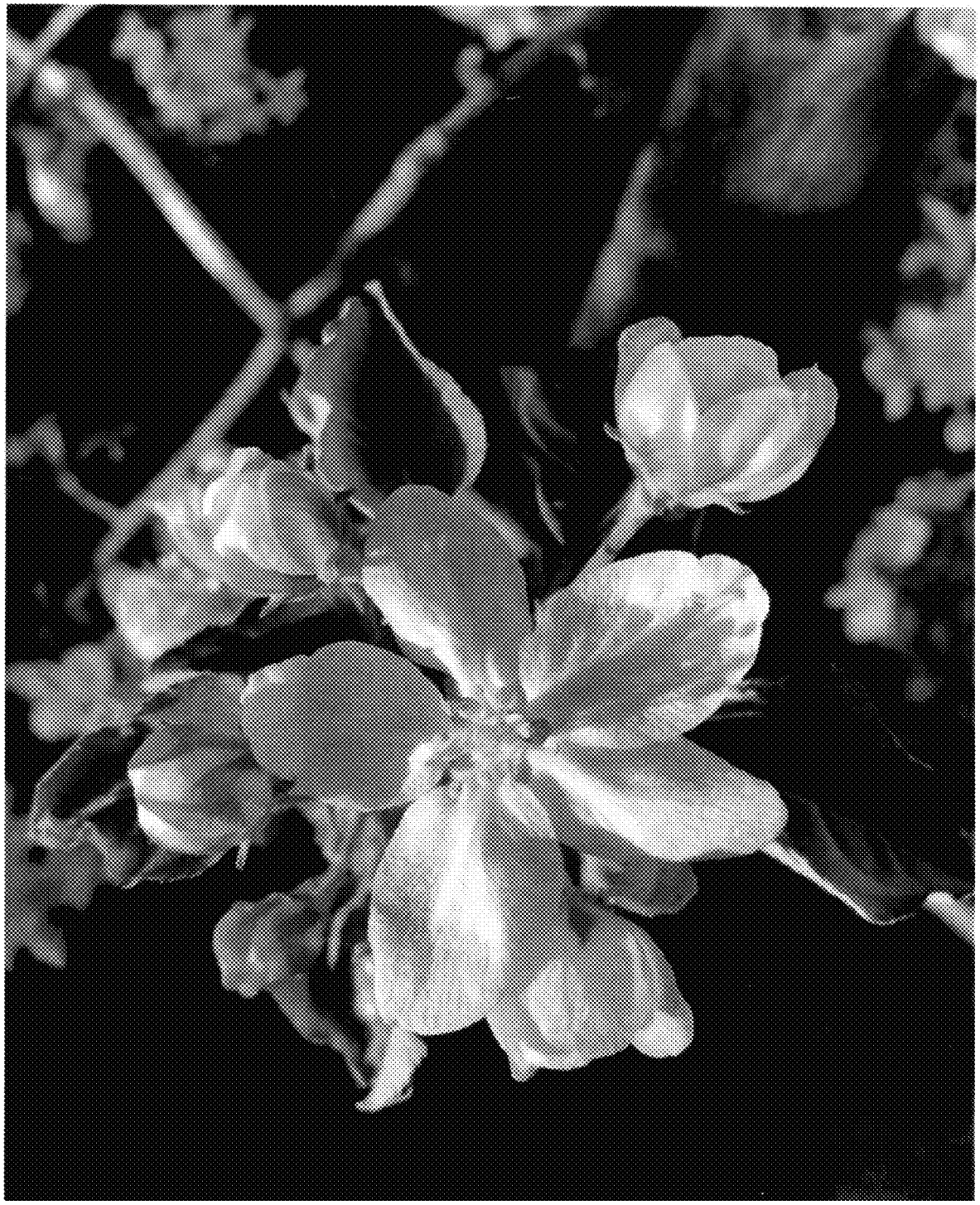
FIG. 2 illustrates blossoms of the new variety showing the pink coloration of buds and blossoms.

A detailed description of the 'SA 1088' cultivar follows using The Royal Horticultural Society of London Colour Chart, 1986 edition, for color identification except where general color terms are sufficient.

Parentage: A whole tree mutation of 'Baigent' (U.S. Plant Pat. No. 10,016). Locality of the original discovery and observations is 2637 7 Mile Road, Comstock Park, MI 49321.

Tree:

*Age.*—11 years.

*Size.*—Large, height 3 m, width 1.5 m.

*Vigor*.—Vigorous, yearly growth averages 1 m.
*Density*.—Medium.
*Form*.—Upright, spreading.
*Production*.—Very productive, averaging 800 bushels per acre.
*Growth type*.—Non-spur.
*Bearing*.—Annual.

Trunk:
*Diameter*.—130 cm at 40 cm above ground level.
*Bark*.—Smooth, color Grey 201B with an undercolor of Grayed Orange 165B.
*Lenticels*.—2 mm to 8 mm in length, 1 mm in width, color Grayed Orange 165C.

Branches:
5 *year old branch*.—50 mm in diameter, color Grayed Orange 172A.
4 *year old branch*.—30 mm in diameter, color Grayed Orange 172A.
3 *year old branch*.—20 mm in diameter, length 30 cm to 40 cm, Grayed Orange 172A.
2 *year old branch*.—15 mm in diameter, length 25 cm to 40 cm, color Grayed Orange 172A.
1 *year old branch*.—6 mm to 10 mm in diameter, length 25 to 40 cm, color Grayed Orange 172B, lenticels 0.1 mm in diameter, round, color Grayed Yellow 162A.

Leaves:
*Arrangement*.—Opposite.
*Size*.—Length 110 mm to 125 mm, width 80 mm to 90 mm.
*Texture*.—Leathery, crisp.
*Form*.—Broadly lanceolate.
*Base*.—Bluntly pointed.
*Apex*.—Bluntly pointed.
*Adaxial surface pubescence*.—None.
*Abaxial pubescence*.—Very fine.
*Adaxial surface color*.—Yellow Green 143B.
*Abaxial surface color*.—Yellow Green 145C.
*Venation*.—Pinnate, 10-12 veins, mainly alternate.
*Mid-vein*.—Yellow Green 151C on upper surfaces, Lower vein exhibits a bright red coloration, Red 45C. blending with Yellow Green 151C.
*Margin*.—Serrate.
*Leaf glands*.—Absent.
*Petiole length*.—30 mm to 45 mm.
*Petiole width*.—2 mm.
*Petiole color*.—Yellow Green 151C on upper surface with Red 45C on lower petiole extending up the mid-vein on most leaves. Petiole base is commonly red colored on all surfaces extending 10 to 12 mm up the petiole.
*Petiole groove*.—None observed.
*Stipules*.—Very fine, at the base of the petiole on almost all leaves.
*Stipule length*.—7 mm.
*Stipule width*.—0.5 mm.
*Stipule color*.—Yellow Green 147B.

Leaf buds:
*Length*.—5 mm.
*Width*.—4 mm.
*Color*.—Grayed Purple 183A.
*Placement on branch*.—Tightly applied to the branch.
*Internode distance*.—30 mm.

Spurs: Present on $2^{nd}$ year and older wood.
*Length*.—6 to 8 mm.
*Width*.—4 to 6 mm.
*Color*.—Grayed Orange 177A.

Flowers: Mid-season bloom, May 13 in Comstock Park, MI.
*Pollination requirements*.—Any diploid variety in the same season except pollen from Golden Delicious or any other Gala sport.
*Presentation*.—Very showy.
*Fragrance*.—Fragrant.

Flowers at popcorn stage:
*Pedicle*.—Length 18 mm to 22 mm, diameter 2 mm.
*Pedicel color*.—Grayed Green 194A.
*Bud*.—Length 9 mm, width 7 mm to 8 mm.
*Bud color*.—Full blush of Red Purple 51B with background of White 155D.

Flowers at full bloom:
*Corolla diameter*.—Large, 75 mm to 85 mm when fully open.
*Number of flowers per cluster*.—3 to 5.
*Petals*.—Arrangement: free. Color: White 155D with a distinct blush throughout of Red Purple 51B. Shape: Broadly ovate, base rounded to abruptly cuneate at junction with receptacle, apex rounded with slight tip. Entire petal is somewhat flat. Basin is 5 mm deep. Margin: straight with very slight ruffling at the apex. Size: length 30 mm to 35 mm, width 20 mm to 25 mm. Texture: firm.
*Pedicel*.—Length 25 mm to 27 mm, width 2 mm, color Yellow Green 145D.
*Sepals*.—5 in number, wedge shaped, sharply pointed, length 5 mm, width 5 mm, color Yellow Green 145D.
*Filaments*.—Length 10 mm to 12 mm, width 0.3 mm, color White 155D at junction with anther.
*Anthers*.—Length 2 mm, width 1 mm, color Yellow 4C.
*Pistil*.—Held slightly lower than anthers in a majority of blossoms.
*Ovary*.—Length 4 mm, width 1.5 mm, pubescent, color Yellow Green 145D.
*Stigma*.—Width 1 mm, pubescent, color Green White 157C.
*Style*.—Length 3 mm, width 1 mm, color Green White 157C.

Fruit: Maturity when described, firm ripe.
*Harvest time*.—September 1 through 5 in Kent County, Michigan, 5 days ahead of parent and other Gala cultivars.
*Size*.—Uniform, axial diameter 8 cm, transverse diameter 7.5 cm.
*Form*.—Globose.
*Cavity*.—Symmetrical, abrupt at base, apex acuminate, depth 1.5 cm, breadth 2 cm, markings none.
*Basin*.—Symmetrical, rounded, wide, breadth 2.5 cm, depth 1.5 cm, markings none.
*Calyx*.—Closed.
*Segments*.—Broadly lanceolate, reflexed from base at apex, approximate.
*Outer surface*.—Pubescent, color Grayed Green 191B.
*Inner surface*.—Pubescent, color Grayed Green 191C.
*Eye*.—Closed.

Skin: Thin, smooth, waxed, glossy.
*General color effect*.—Bright red blush over 95% to 100% of the fruit, color Red 47A.
*Background color*.—Yellow 8 C.
*Dots*.—Round, 1 mm in diameter, scattered throughout surface, color Yellow 8B.
*Flesh*.—Juicy, satiny.
*Color*.—Yellow Orange 19D.

*Texture*.—Firm, tender, fine, crisp.
*Flavor*.—Sweet, aromatic.

Core:
*Bundle area*.—Small, oblate.
*Bundles*.—Inconspicuous, in one whorl.
*Core lines*.—Clasping, indistinct.
*Calyx-tube*.—Funnel form, glabrous toward base.
*Stem of funnel*.—Long.
*Depth of tube to shoulder*.—9 mm.
*Entire depth*.—21 mm.
*Auxiliary cavity*.—Present.
*Seed cells*.—Axial, open.
*Cell walls*.—Thin.
*Length*.—16 mm.
*Breadth*.—6 mm.
*Longitudinal section*.—Orbicular, obtuse at apex.
*Surface*.—Smooth.
*Cross section*.—Broad.

Seeds:
*Number perfect*.—6 to 10.
*Number in one cell*.—2.
*Length*.—7 mm.
*Breadth*.—4 mm.
*Color*.—Brown 199A.

Stem: Length 2.5 cm, breadth 6 mm at head decreasing to 4 mm at base, clubbed 210 at head.
*Color*.—172C.

Use: Processing, fresh market, dessert.

Shipping quality: Good, subject to stem puncture.

Keeping quality: Excellent, 90 to 120 days in common storage, 6 months in controlled atmosphere storage.

Tree winter hardiness: Average for an apple variety. Tree is hardy to −20° to −25° F.

Bud winter hardiness: −10° to −15° F., depending on the stage of development of the bud.

Drought tolerance: Average for an apple variety. Normal requirements average ½" of rain per week. Severe drought adversely affects fruit size and quality.

Disease resistance: susceptible to fire blight (*Erwinia amylovora*) and other bacterial diseases. Moderately susceptible to apple scab (*Venturia inaequalis*), powdery mildew (*Podosphaera leucotricha*), and other fungal diseases.

Chilling requirement: 600 to 800 hours.

I claim:

1. A new and distinct variety of apple tree named 'SA 1088', substantially as herein shown and described.

* * * * *